(12) United States Patent
Fojtik (10) Patent No.: US 11,896,508 B2
(45) Date of Patent: *Feb. 13, 2024

(54) EXPANDABLE EXOSKELETON DEVICES

(71) Applicant: Transit Scientific, LLC, Salt Lake City, UT (US)

(72) Inventor: Shawn P. Fojtik, Park City, UT (US)

(73) Assignee: Transit Scientific, LLC, Salt Lake City, UT (US)

( * ) Notice: Subject to any disclaimer, the term of this patent is extended or adjusted under 35 U.S.C. 154(b) by 742 days.

This patent is subject to a terminal disclaimer.

(21) Appl. No.: 16/579,770

(22) Filed: Sep. 23, 2019

(65) Prior Publication Data

US 2020/0093618 A1  Mar. 26, 2020

Related U.S. Application Data

(60) Provisional application No. 62/735,110, filed on Sep. 22, 2018.

(51) Int. Cl.

| A61F 2/06 | (2013.01) |
|---|---|
| A61F 2/07 | (2013.01) |
| A61B 17/00 | (2006.01) |
| A61M 25/00 | (2006.01) |
| A61F 2/90 | (2013.01) |
| A61F 2/958 | (2013.01) |

(Continued)

(52) U.S. Cl.
CPC ........ *A61F 2/90* (2013.01); *A61B 17/320725* (2013.01); *A61F 2/958* (2013.01); *A61F 2002/825* (2013.01); *A61F 2250/0067* (2013.01); *A61F 2250/0098* (2013.01)

(58) Field of Classification Search
None
See application file for complete search history.

(56) References Cited

U.S. PATENT DOCUMENTS 5,637,113 A * 6/1997 Tartaglia .................. A61F 2/92
623/1.42
10,863,997 B2 * 12/2020 Enami .................... A61B 17/22
(Continued)

FOREIGN PATENT DOCUMENTS

| JP | 2007530213 A | 11/2007 |
|---|---|---|
| JP | 2008036076 A | 2/2008 |

(Continued)

OTHER PUBLICATIONS

Japan Patent Office, "Office Action," Japanese Application No. 2021-516483, dated Apr. 22, 2022.
(Continued)

*Primary Examiner* — Ann Schillinger
(74) *Attorney, Agent, or Firm* — DENTONS Durham Jones Pinegar (57) ABSTRACT

An exoskeleton device includes an expandable section. The expandable section may be positioned over an expander, such as a balloon catheter, and expand upon expansion of the expander. The expandable section may include struts that rotate as the expandable section expands. Edges of the struts may score surfaces (e.g., pathology, tissue, etc.) against which the struts are forced as the expandable element expands. The expandable element may carry a medicament, which may be delivered upon expansion of the expandable element.

15 Claims, 6 Drawing Sheets

(51) Int. Cl.
*A61B 17/3207* (2006.01)
*A61F 2/82* (2013.01)

(56) References Cited

U.S. PATENT DOCUMENTS

| | | | |
|---|---|---|---|
| 11,179,549 B2* | 11/2021 | Fojtik | A61M 25/104 |
| 11,406,801 B2* | 8/2022 | Fojtik | A61B 17/320725 |
| 2002/0065546 A1* | 5/2002 | Machan | A61F 2/07 623/1.36 |
| 2003/0181973 A1* | 9/2003 | Sahota | A61L 31/16 623/1.42 |
| 2005/0154448 A1* | 7/2005 | Cully | A61F 2/07 623/1.15 |
| 2005/0171593 A1* | 8/2005 | Whirley | A61F 2/07 623/1.42 |
| 2005/0182474 A1* | 8/2005 | Jones | A61F 2/90 623/1.11 |
| 2006/0271093 A1* | 11/2006 | Holman | A61M 25/10 606/194 |
| 2007/0255388 A1 | 11/2007 | Rudakov et al. | |
| 2009/0240270 A1* | 9/2009 | Schneider | A61M 25/104 606/198 |
| 2011/0082483 A1* | 4/2011 | Diamant | A61B 17/22032 139/11 |
| 2014/0004169 A1 | 1/2014 | Falotico et al. | |
| 2015/0209165 A1 | 7/2015 | Grandfield et al. | |

FOREIGN PATENT DOCUMENTS

| | | | |
|---|---|---|---|
| JP | 2009183740 A | | 8/2009 |
| JP | 2017-506941 A | | 3/2017 |
| JP | 2018099485 A | * | 6/2018 |
| JP | 2018099485 A | | 6/2018 |
| WO | 2017049227 A2 | | 3/2017 |

OTHER PUBLICATIONS

European Patent Office, "Extended European search report," European Application No. 19863410.7, dated May 19, 2022.

USPTO as International Searching Authority, "International Search Report and Written Opinion," International application No. PCT/US2019/052510, dated Nov. 13, 2019.

Japan Patent Office, "Office Action," Japanese Application No. 2021-516483, dated Feb. 7, 2023.

* cited by examiner

EXPANDABLE EXOSKELETON DEVICES

CROSS-REFERENCE TO RELATED APPLICATION

A claim for the benefit of the Sep. 22, 2018 filing date of U.S. Provisional Patent Application 62/735,110, titled ELONGATED EXOSKELETON ELEMENT FOR USE OVER ELONGATED MEDICAL INSTRUMENTS ("the '110 Provisional Application") is hereby made pursuant to 35 U.S.C. § 119(e). The entire disclosure of the '110 Provisional Application is hereby incorporated herein.

TECHNICAL FIELD

This disclosure relates generally to exoskeleton devices for use on the outer surfaces of elongated medical instruments, such as catheters and balloons (e.g., angioplasty balloons, etc.). More specifically, this disclosure relates to exoskeleton devices that can be expanded in a manner that enables the exoskeleton devices to score tissues, plaques, or other targets against which the expanded exoskeleton devices are forced. Even more specifically, exoskeleton devices according to this disclosure may include features that facilitate scoring and/or the delivery of drugs to their target locations.

RELATED ART

Percutaneous transluminal angioplasty (PTA), which is commonly referred to as balloon angioplasty or, even more simply, as angioplasty, is a commonly used minimally invasive endovascular procedure for treating vessels (e.g., arteries, veins, etc.) whose pathways have been narrowed or obstructed (i.e., stenosis of the vessels). As a non-limiting example, angioplasty is often used to surgically treat arterial atherosclerosis (i.e., the formation of plaques on the insides of arterial walls)—a common cause of stenosis. Angioplasty typically involves introducing a deflated balloon catheter to the narrowed or obstructed portion of the vessel, which may be visually confirmed by fluoroscopy, and then inflating the balloon to force the obstructed or narrowed portion of the vessel, including the atherosclerosis, outward. A stent may be placed at that site to hold the newly revascularized portion of the vessel open. Atherosclerosis or, more specifically, the atherosclerotic plaque typically remains in place following angioplasty.

Some PTA and percutaneous transluminal coronary angioplasty (PTCA) balloon catheters include scoring blades. Some examples of such scoring balloon catheters include those marketed under the AngioSculpt trademark by the Philips Healthcare division of Koninklijke Philips N.V. Upon introducing the balloon of such a device to a treatment site within a blood vessel of a subject and then expanding the balloon, the scoring blades engage the inner surface of the blood vessel and score it. Currently available scoring balloon catheters, such as AngioSculpt® scoring balloon catheters, only include three (3) blades, limiting the number of scores marks or cuts that may be made by inflating the balloon once—a single pass. Thus, such a device may not provide an improvement in the effectiveness with which a drug is delivered to and treats the scored tissue. Such a device is typically rotated and re-inflated more than once to provide a more effective number of score marks in the tissue. Nevertheless, the depth of each score is limited by the distance the scoring blades protrude beyond the exterior surface of the balloon, with no currently available scoring balloon catheter providing a score depth of more than about 0.25 mm, which may not be aggressive enough to effectively deliver drugs into the scored tissue.

Angioplasty may be accompanied by treatment with medicines, but that treatment is typically limited to drugs that are not administered to the subject until after the angioplasty procedure has been completed. The administration of such drugs may continue for a prolonged duration. As an example, treatment with medicines that prevent or treat blood clots (e.g., acetylsalicylic acid (aspirin), an antiplatelet medication (clipidogrel), etc.) may continue for several months (e.g., three months, six months, one year, etc.) or even indefinitely after angioplasty and/or stent placement.

SUMMARY

An exoskeleton device according to this disclosure is capable of assembly with a balloon catheter. More specifically, an expandable section of an exoskeleton device may include a lumen that can receive a balloon catheter, including an expandable element of the balloon catheter. The expandable section of the exoskeleton device, or at least a portion of the expandable section, may be capable of expanding, for example, upon expansion (e.g., inflation, etc.) of an expandable element of a balloon catheter over which that portion of the expandable section is positioned. When the expandable section of an exoskeleton device expands, it may be capable of being forced against and scoring an adjacent surface (e.g., a surface of a plaque on an inner surface of a vessel, an inner surface of a vessel, etc.). The expandable section may include a plurality of struts, or spines, positioned around a circumference of the expandable section. Each strut may extend along a length of the expandable section. As the expandable section or a portion thereof expands (e.g., under force of a balloon, under tension, etc.), each arcuate (but substantially flat) strut may rotate (e.g., by about 90°, etc.), causing an edge or a corner of the edge to move from a circumferential orientation to a more radial orientation.

In a specific embodiment, the expandable section may comprise a hypotube, which may be formed from a substantially rigid material, such as a metal (e.g., stainless steel, nitinol, etc.) or a polymer (e.g., polyether ether ketone, etc.). The struts may be defined by laser cutting. Adjacent rows of slits may be defined, with the slits of each row being offset from the slits of an adjacent row. Each row of slits may be positioned along a generator of the expandable section (i.e., a line extending from one end of the expandable section to the other end of the expandable section, parallel to an axis of the expandable section). Each slit may overlap about half of one (if the slit is located at or near an end of the hypotube) or two (if the slit is intermediately located) slits of an adjacent row; stated another way, the slits of an expandable section may have a so-called "brickwork" arrangement, or they may be arranged like the bricks in a so-called "running bond pattern." Such an arrangement may enable a portion of each strut to rotate (e.g., by about 90°, etc.) (or cause rotation of that portion of the strut) upon expansion of a portion of the expandable section on which that strut is located or placement of that strut under tension. Such an arrangement may also cause an expanded portion of the expandable section to resiliently return substantially to its relaxed state once an internal force on that portion of the expandable section is released (e.g., when pressure from an expandable element of a balloon catheter within the expandable section is released, etc.). Thus, there is no need for a separate resilient element on or within the expandable section. With such an arrangement, when the expandable section is in a relaxed state, or an unexpanded state, it may have a smooth outer surface.

When in a radially disposed orientation, the edge or corner of each strut may engage and/or score a surface against which the strut is forced.

The expandable section may include features that enhance the manner in which it engages the features (e.g., pathology, such as plaques, lesions, etc.; tissue; etc.) against which the expandable section is positioned upon its expansion. An edge of a strut that will face radially, or outward, as the strut rotates may be sharpened, serrated, or otherwise finished in a manner that will enhance an ability of the strut to score a surface (e.g., pathology, tissue, etc.) against which the strut is forced. The scoring profile of each rotated strut may correspond to the thickness of the outer wall of the exoskeleton device, in which the struts are defined. As a nonlimiting example, the struts defined from a 0.0025 inch thick outer wall will have cutting profiles of 0.0025 inch when the expandable section of the exoskeleton device is in its expanded state. The scoring depth of each rotated strut may correspond to the distance across, or width, of the strut. As a nonlimiting example, a strut having a width of about 0.020 inch (about 0.50 mm) may penetrate a surface to a depth of up to about 0.020 inch (about 0.50 mm); a strut having a width of about 0.03 inch (about 0.75 mm) may penetrate a surface to a depth of up to about 0.030 inch (about 0.75 mm); etc.

As an alternative to struts with a sharp edges and/or corners, an exoskeleton device according to this disclosure may include struts with corners that are smooth (e.g., burnished, etc.) or rounded. Such a configuration may enable the struts, when forced radially and rotated, to engage and even atraumatically score a surface against which the strut is forced (e.g., tissue, pathology, etc.).

One or more corners and/or the edge of a strut that faces outwardly upon rotation of the strut may have a smooth finish, or their surface(s) may be textured in a manner that enables them to better engage and/or score a surface against which they are positioned as the strut is forced radially outward and rotates into its engaging position.

The expandable section of the exoskeleton device may also include other configurations of slits and struts.

The expandable section may include features that safely and effectively deliver drugs or other substances to target locations within a subject's body, including, without limitation, to the features against which the expandable section is positioned upon its expansion.

Placement of the medicament or other substance may prevent it from being shed or sheered from the exoskeleton device as the exoskeleton device is introduced to a desired location with a subject's body, while the struts are in the original, unexpanded, unrotated positions. Upon expanding the expandable section, or a portion thereof, to cause one or more struts of the exoskeleton device to rotate outward such that its edge or their edges engage (e.g., contact, score, etc.) a surface (e.g., pathology, tissue, etc.), the exoskeleton device may deliver the medicament or other substance to the surface. In some embodiments, the expandable section of the exoskeleton device may carry a medicament or another substance on edges of its struts that will rotate outwardly upon expansion of the expandable section. Alternatively, or in addition, medicament or another substance may be carried by inner surfaces of the struts, adjacent to the edges that will rotate outwardly upon expansion of the expandable section. The medicament or other substance may be carried directly by edges and/or surfaces of the struts (e.g., in solid form, within recessed areas of textured surfaces, within pores, etc.) or indirectly by carriers (e.g., an absorbent element, a hydrogel, etc.) on edges and/or surfaces of the struts. The medicament or other substance may be delivered to a surface within a subject's body as the struts of the expandable section of the exoskeleton device are forced radially outward (e.g., into contact with pathology, tissue, etc.; as they score the pathology, the tissue, etc.; etc.).

As an alternative to having the struts carry the medicament or another substance, the expandable element may include a polymeric film that carries the medicament or other substance. As an example, one or more porous polymeric films may surround the exterior surfaces of the unrotated, or relaxed, struts, internally line the unrotated struts, and/or be located between adjacent struts (e.g., spaced apart struts, etc.). Such a porous polymeric film may include pores that carry and retain the medicament or other substance while the porous polymeric film remains in a relaxed state, but release the medicament or other substance when the struts are forced radially outward and the porous polymeric film is stretched.

In addition to the expandable section, the exoskeleton device may also include a collar around a distal end of the expandable section, as well as a tubular element (e.g., a catheter, an extension of the expandable section, etc.) coextensive with a proximal end of the expandable section. The collar may comprise a smooth, even flexible member. Among other functions, the collar may facilitate introduction of the exoskeleton device into the body of a subject and/or prevent expansion of a distal end of the expandable section. In a specific embodiment, the collar or the distal end of the exoskeleton device may have a 5° taper to facilitate its introduction into a subject's body, i.e., to improve its crossability. The tubular element may include a lumen that can receive a balloon catheter and, thus, enable placement of the exoskeleton device on the balloon catheter.

Alternatively, the expandable portion (i.e., the struts) of an exoskeleton device according to this disclosure may extend to the distal end of the exoskeleton device. Such a configuration may enable the distal end to be expanded (e.g., to the shape of a funnel and, thus, use of the distal end of the exoskeleton device as a funnel). The inclusion of an expandable film around the expandable portion of the exoskeleton device may impart the expandable portion with further functionality (e.g., to enable use of a distal end of the expandable section, such as a distal end that has been expanded into the shape of a funnel, to aspirate material, etc.). The exoskeleton device, or at least its expandable portion, and any expandable film surrounding the expandable portion of the exoskeleton device may be capable of retaining their expanded shapes (e.g., funnel shapes, etc.) into which they are formed. These may include the use of some metals, metal alloys, or polymers for use in forming the expandable portion and some stretchable polymers and/or polymers or fabrics that may be alternately gathered and held taught for use in forming the expandable film.

An exoskeleton device may be capable of use over an entirety (or substantially an entirety) of a balloon catheter or it may be configured as a rapid exchange device. Such an embodiment of exoskeleton device may comprise a catheter. Complete and rapid exchange embodiments of an exoskeleton device may be used with standard balloon catheter. Alternatively, an exoskeleton device according to this disclosure may be configured for and/or capable of use on a rapid exchange balloon catheter.

In another aspect, a medical system is disclosed. A medical system according to this disclosure includes an exoskeleton device and a balloon catheter, and may also include a guide wire. The exoskeleton device may be capable of placement over the balloon catheter, or of receiving at least a portion of the balloon catheter, including an expandable element of the balloon catheter. Any embodiment of exoskeleton device according to this disclosure may be included in a medical system with a balloon catheter. The balloon catheter may have any configuration suitable for the procedure to be performed using the medical system. If a guide wire is included in the medical system, it may have a size (e.g., an outer diameter) suitable for use with the selected balloon catheter.

In addition to an exoskeleton device, a balloon catheter, and an optional guide wire, a medical system may include apparatuses that facilitate introduction of the guide wire, the balloon catheter, and/or the exoskeleton device into the body of a subject, apparatuses that work in conjunction with the balloon catheter, imaging apparatuses, medicaments, and the like.

According to another aspect, methods for using an exoskeleton device according to this disclosure may include the introduction of a balloon catheter into a subject's body. The balloon catheter may be introduced, or advanced, into the subject's body along a guide wire that was previously placed along a desired path within the subject's body. While advancing the balloon catheter into the subject's body, an expandable element of the balloon catheter may be advanced to a location within the subject's body that is to be treated (e.g., to a plaque in a blood vessel, to a clot, to a diseased or an injured location of a blood vessel, etc.).

An exoskeleton device may be positioned over the balloon catheter. In some embodiments the exoskeleton device may be positioned over the balloon catheter before the balloon catheter is introduced into the subject's body. In other embodiments, the exoskeleton device may be introduced, or advanced, into the subject's body along a balloon catheter that was previously placed along the desired path within the subject's body. Positioning of the exoskeleton device over the balloon catheter may include placement of an expandable section of the exoskeleton device over an expandable element of the balloon catheter. If necessary, the positions of the expandable section of the exoskeleton device and the expandable element of the balloon catheter may be modified relative to a location that is to be treated within the subject's body. The relative positions of the expandable section of the exoskeleton device and the expandable element of the balloon catheter may be adjusted.

With the expandable section of the exoskeleton device and the expandable element of the balloon catheter at desired locations within a subject's body, the expandable element of the balloon catheter may be inflated. Inflation of the expandable element of the balloon catheter may cause the expandable section of the exoskeleton device to expand. Expansion of the expandable section of the exoskeleton device may force members of the expandable section, such as struts against the location that is to be treated. As the members of the expandable section are forced against the location that is to be treated, the members of the expandable section may contact and, optionally, score that location. In some embodiments, an electrical current may be applied to the exoskeleton device and, thus, to its struts to cauterize tissue or pathology contacted by the struts. In embodiments where the members of the expandable section carry a medicament, the medicament may be transferred to the location that has been treated and introduced into any scores formed at that location.

In another embodiment of a method for performing a medical procedure, a guide wire may be introduced into a subject's body, with a distal end of the guide wire being located at a target location within the body of the subject. An exoskeleton device according to this disclosure (e.g., an exoskeleton device that comprises a catheter) may be introduced into the body over the guide wire. With the exoskeleton device in place within the subject's body, the guide wire may be removed and the medical procedure may be conducted using (e.g., through, etc.) the exoskeleton device. In a specific embodiment, a balloon catheter may be introduced into the subject's body through the exoskeleton device. Once in place, the balloon of the balloon catheter may be expanded to expand the expandable element of the exoskeleton device. Expansion of the expandable element may enable the scoring of tissues against which struts of the exoskeleton device are positioned and, optionally, the delivery of a therapeutic agent (e.g., a drug, etc.) to the scored surfaces, the delivery of other substances to the target location within the subject's body, the break-up of materials at the target location, and/or the aspiration of material(s) from the target location.

An exoskeleton device that incorporates teachings of this disclosure may be used in a variety of procedures, including without limitation in angioplasty and similar procedures, in pyeloplasty procedures, in tuboplasty procedures, in procedures in nasal passages and sinuses, in procedures in biliary ducts, and in gastrointestinal (e.g., esophageal, intestinal, etc.) procedures.

Once the desired treatment of a location is complete, the expandable element of the balloon catheter may be deflated, enabling the expandable section of the exoskeleton device to transition from an expanded state to an unexpanded state. The expandable section of the exoskeleton device and the expandable element of the balloon catheter may then be moved (e.g., advanced, withdrawn, etc.) to another location that is to be treated. Alternatively, the exoskeleton device and the balloon catheter may be removed from the subject's body.

Other aspects of the disclosed subject matter, as well as features and advantages of various aspects of the disclosed subject matter, will become apparent to those of ordinary skill in the art through consideration of the foregoing disclosure, the accompanying drawings and images, and the appended claims.

DETAILED DESCRIPTION

An embodiment of an exoskeleton device 10 according to this disclosure is depicted by FIGS. 1-8. The exoskeleton device 10 comprises an elongated medical device with an expandable section 30. The exoskeleton device 10 is at least partially defined by a body 12 that includes a distal portion 16, and intermediate portion 18, and a proximal portion 20.

At least part of the distal portion 16 of the body 12 of the exoskeleton device 10 may have a tubular configuration, through which a lumen 14 is defined. In the depicted embodiment, the body 12 has a tubular configuration along its entire length; thus, the lumen 14 extends through the entire length of the body 12.

The body 12 may comprise a substantially unitary structure or it may include a plurality of assembled elements that have been secured together. In embodiments where the body 12 includes a substantially unitary structure, it may be defined from a single element (e.g., a tube, etc.). An embodiment of the body 12 that includes a plurality of assembled elements may include a distal portion 16 that is formed separately from and subsequently assembled with and joined to a remainder of the body 12, including its intermediate portion 18 and its proximal portion 20.

The body 12 may be formed from any of a variety of suitable materials or from a combination of suitable materials. In some embodiments, the entire body 12 or its distal portion 16 may be defined from or comprise a hypotube, which may be formed from a substantially rigid material, such as a metal. Examples of suitable metals include, but are not limited to stainless steel (e.g., 316L stainless steel, 316 stainless steel, etc.), memory metals (e.g., nitinol, etc.), cobalt chromium (CoCr), nickel chromium (NiCr or nichrome) alloys (including, without limitation, NiCr steel), and the like. Alternatively, the body 12 may be formed from a polymer. A suitable polymer may have a sufficient hardness (e.g., at least 35 Shore D, 35 Shore D to 55 Shore D, 35 Shore D to 72 Shore D, etc.). Examples of suitable polymers include, but are not limited to polyether ether ketone (PEEK), polyimide, nylon, polyether block amides (PEBA, such as that branded as PEBAX®), and extruded plastics (provided that they have a wall 13 thickness that does not exceed the width of their struts 36, as explained below). In embodiments where the body 12 comprises a distal portion 16 that has been formed separately from a remainder of the body 12, the remainder of the body 12 may be formed from any of a variety of suitable materials, including, without limitation, materials from which catheters may be formed (e.g., silicone, nylon, polyurethane, polyethylene, polyethylene terephthalate (PET), polytetrafluoroethylene (PTFE), latex, etc.), as well as a variety of other materials.

The expandable section 30 of the exoskeleton device 10 may be capable of expanding outward (e.g., radially outward, etc.) from an unexpanded state, as shown in FIGS. 1-4, to an expanded state, as depicted by FIGS. 5-8, upon applying an expanding force (e.g., a radially outwardly expanding force, etc.) from within the expandable section 30 to inner surfaces $13_I$ of the wall 13 of the portion of the body 12 from which the expandable section 30 is defined. The expandable section 30 may be capable of resiliently returning or substantially resiliently returning to the unexpanded state upon removal of the expanding force.

The expandable section 30 of the exoskeleton device 10 may, as illustrated, be located along the distal portion 16 of the body 12 of the exoskeleton device 10. A distal side of the expandable section 30 may be positioned adjacent to a distal end 15 of the body 12. Exoskeleton devices with expandable sections that are located at other positions (e.g. more proximal positions) along the lengths of the bodies of the exoskeleton devices (e.g., along at least part of the intermediate portion 18, along at least part of the distal portion 16, etc.) are also within the scope of this disclosure.

The expandable section 30 may comprise, or be defined by, at least part of the body 12 of the exoskeleton device 10. In the embodiment of exoskeleton device 10 illustrated by FIGS. 1 and 6, the expandable section 30 is defined by series 34a, 34b, 34c, etc., of slits 32 that extend at least partially through a wall 13 of the body 12. In some embodiments, each slit 32 may extend completely through the wall 13 of the body 12, from its outer surface $13_O$ to its inner surface $13_I$. In other embodiments, each slit 32 may extend only partially through the wall 13 of the body 12 (e.g., from the outer surface $13_O$ of the wall 13 toward the inner surface $13_I$ of the wall 13, etc.). The extent to which each slit 32 extends through the wall 13 of the body 12 may depend, at least in part, upon the material from which the body 12 is formed.

In some embodiments, the cut(s) that define(s) each slit 32 may extend radially through the wall 13 (i.e., toward a longitudinal axis 31 of the expandable section 30). A radially oriented cut may impart the slit 32 with edges that are square or substantially square and that include substantially perpendicular corners.

The slits 32 (and any other embodiment of slit) may be formed by any technique that is compatible with the material from which the body 12 of the exoskeleton device 10 is formed. As a non-limiting example, laser cutting processes may be used to form slits 32 in the body 12.

Each series 34a, 34b, 34c, etc., may be defined by linearly aligned slits 32. The slits 32 and each series 34a, 34b, 34c, etc., may extend longitudinally along the body 12, with each series 34a, 34b, 34c, etc., being positioned along a generator of the expandable section 30 (i.e., a line extending from one end of the expandable section 30 to the other end of the expandable section 30, parallel to a longitudinal axis 31 of the expandable section 30). Such an orientation may be referred to as a "straight" orientation. As will be described in further detail hereinafter, exoskeleton devices with other orientations of slits are also within the scope of this disclosure.

Adjacent slits 32 in a series 34a, 34b, 34c, etc., are spaced apart by solid, uncut regions of the body 12. These solid regions may be referred to as joints 38 or junctions. The distance across these joints 38, or across the solid regions between adjacent slits 32 in a series 34a, 34b, 34c, etc., may be referred to as the "junction length." The junction length may be tailored to enable expansion of the expandable section 30 and to avoid failure as the expandable section 30 expands. In a specific but nonlimiting embodiment, the junction length between adjacent slits 32 in a series 34a, 34b, 34c, etc., and, thus, across each joint 38 may be 0.014 inch (0.36 mm).

The slits 32 of each series 34b, 34c, 34d, etc., may be offset relative to the slits 32 of each adjacent series 34a, 34b, 34c, 34d, 34e, etc. Each slit 32 in a series 34a, 34b, 34c, etc., may overlap about half of one (if the slit 32 is located at or near an end of the expandable section 30) or two (if the slit 32 is intermediately located along the length of the expandable section 30) circumferentially adjacent slits 32 of each adjacent series 34a, 34b, 34c, etc. Staggering of the slits 32 around the circumference of the distal portion 16 of the body 12 of the exoskeleton device 10 may provide the expandable section 30 with a so-called "brickwork" appearance, with solid portions of the body 12 between the slits 32 arranged in a so-called "running bond pattern." In some embodiments, circumferentially corresponding slits 32 of every other series 34a and 34c, etc., of slits 32 may have equal lengths and be in complete alignment. All of the slits 32 of a circumferentially aligned series 34a, 34b, 34c, etc., of slits 32 may have the same length. In some embodiments, with the exception of smaller slits 32 (e.g., half-length slits 32, etc.) at the ends of an expandable section 30, all of the slits 32 of the expandable section 30 may have the same length. In other embodiments, the length of the slits 32 of one circumferentially aligned series 35a may differ from the length of the slits 32 of another circumferentially aligned series 35b. NEW FIG.

Circumferentially adjacent series 34a, 34b, 34c, etc., of slits 32 may be spaced equidistantly around the circumference of the body 12. The expandable section 30 may include an even number of series 34a, 34b, 34c, etc., of slits 32. In embodiments where an even number of circumferentially adjacent series 34a, 34b, 34c, etc., of slits 32 are spaced equidistantly around the circumference of the body 12, each slit 32 of the expandable section 30 may be staggered relative to its circumferentially adjacent slits 32. Alternatively, the distance between slits 32 of one circumferentially adjacent series 34a may differ from the distance between slits 32 of another circumferentially adjacent series 34c; thus, the number of slits 32 of one circumferentially adjacent series 34a may differ from the number of slits 32 of another circumferentially adjacent series 34c.

The slits 32 (with the exception of some slits 32 located at the ends of the expandable section 30) may have the same lengths as one another.

The solid portions of the body 12 that are located between each adjacent pair of series 34a and 34b, 34b and 34c, 34c and 34d, etc., of slits 32 comprise struts 36 of the expandable section 30. More specifically, each strut 36 may comprise a solid portion of the body 12 between adjacent series 34*a* and 34*b*, 34*b* and 34*c*, 34*c* and 34*d*, etc., of slits 32. Stated another way, each slit 32 comprises a gap between a pair of circumferentially adjacent struts 36.

Staggering of the slits 32 may enable the expandable section 30 to expand, as described in further detail below with reference to FIGS. 5 and 6-8. In some embodiments, as the expandable section 30 expands, the struts 36 may rotate. Such rotation may occur, for example, in embodiments where each ring of circumferentially aligned struts 36 around an expandable section 30 includes an even number of struts 36. As the slits rotate, they protrude outwardly (e.g., radially, etc.) from the circumference of the expandable section 30.

The width of each strut 36 may correspond to the distance the outwardly turned edge of the strut 36 may protrude into a surface (e.g., tissue, etc.) against which it is forced. For example, a strut 36 with a width of about 0.25 mm may be considered to be "less aggressive," a strut 36 with a width of about 0.50 mm may be considered to be "medium" in terms of aggressiveness, and a strut 36 with a width of about 0.75 mm may be considered to be aggressive.

Figure 3:
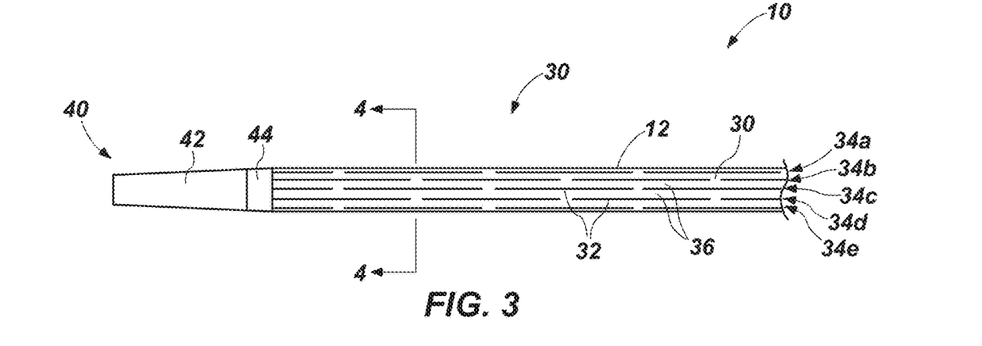
FIG. 3 provides an enlarged side view of the expandable section of the exoskeleton device in the unexpanded state.
Figure 3A:
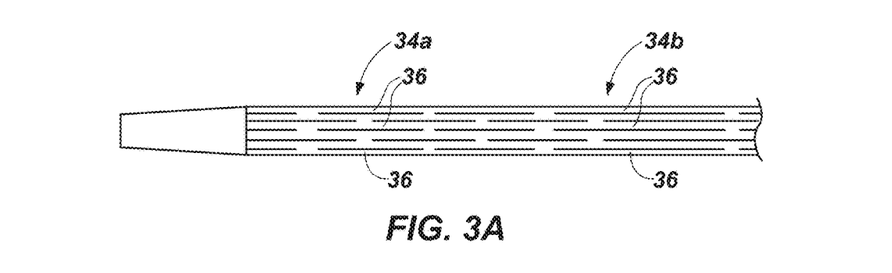
FIG. 3A provides an enlarged side view of another embodiment of expandable section of an exoskeleton device, with the expandable section in an unexpanded state.
Figure 4:
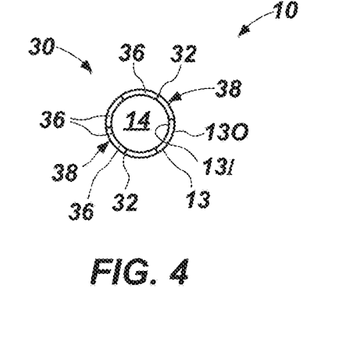
FIG. 4 provides a circumferential cross-sectional view through the expandable section in the unexpanded state, taken along line 4-4 of FIG. 3.

As shown in FIG. 3A, the struts 36 of one circumferentially adjacent series 34*a* may have a width that differs from a width of the struts of another circumferentially adjacent series 34*c*. Such variable strut width may impart different circumferential portions of an expandable section 30 with flexibilities and/or stiffnesses that differ from one another.

The length of each strut 36 may correspond somewhat to its width. The length of each strut 36 should, however, be short enough to enable the strut 36 to rotate as the expandable section 30 expands. The length of each strut 36 may also be a function of the outer diameter of the body 12 and, thus, the relaxed outer diameter of the expandable section 30. As an example, a strut 36 may have a length of about 4 mm to about 5 mm. Of course, expandable sections 30 with larger outer diameters (e.g., 9F, greater than 9F, etc.) may include longer struts (e.g., about 4 mm long to about 9 mm long).

The features that define an expandable section 30 may be tailored. More specifically, the features that define the expandable section 30 may be tailored to impart an expandable section 30 with one or more desired properties. Such tailoring, as well as the resulting properties of the expandable section 30, may be based on the material from which the body 12 of the exoskeleton device 10 is formed, on the dimensions of the body 12 (e.g., the thickness of its wall 13, its inner diameter, its outer diameter, etc.), other factors that may affect the properties of the expandable section 30, or any combination of factors that may affect the properties of the expandable section 30. As an example, the expandable section 30 may include features that impart it with desired amounts of expandability and lateral flexibility, deformability (e.g., struts 36 that rotate to a desired extent upon expansion of the expandable section 30, etc.), and the ability to return to substantially its original shape (i.e., non-plastic deformation and resilience). Without limitation, the number of slits 32 around the circumference of the body 12 (and, thus, the distance between circumferentially adjacent slits 32), the length of each slit 32, and/or the shape of each slit 32 may, individually or in combination, define an expandable section 30 that has desired levels of expandability, lateral flexibility or rigidity, deformability, and resilience.

The extent to which the struts 36 of an expandable section 30 rotate upon expansion of the expandable section 30 depends in part upon the material from which the body 12 of the exoskeleton device 10 is formed and in part upon the extent to which the slits 32 are opened upon expanding the expandable section 30. As an example, a strut 36 may start to rotate when expansion of an expandable section 30 opens the ends of the slits 32 that define the strut 36 by angles of at least about 5° to at least about 15°.

The extent to which the shape of an expandable section 30 is plastically deformed following expansion and release of an expanding force also depends in part upon the material from which the body 12 of the exoskeleton device 10 is formed and in part upon the extent to which the slits 32 are opened upon expanding the expandable section 30. As an example, plastic deformation of the expandable section 30 may not occur until expansion of an expandable section 30 opens the ends of the slits 32 to angles of at least about 25° to at least about 40°.

In embodiments where the body 12 comprises a hypotube formed from 316L stainless steel, the struts 36 will rotate when the expandable section 30 is expanded enough to cause the ends of the slits 32 to open to an angle of at least about 10°. As long as the ends of the slits 32 open to an angle of less than about 30°, the struts 32 may rotate back to their original positions and the expandable section 30 may return to substantially its original shape upon releasing an expanding force from the expandable section 30. Thus, provided expansion of the expandable section 30 only opens the ends of the slits 32 to angles of about 10° to less than about 30°, the struts 36 may rotate outwardly and the expandable section 30 may resiliently return to substantially its original shape. If the expandable section 30 is expanded in a manner that causes the ends of the slits 32 to open by more than about 30°, the expandable section 30 may be plastically deformed, which may prevent the struts 36 from rotating back to their original positions and the expandable section 30 from returning to substantially its original shape.

Figure 5:
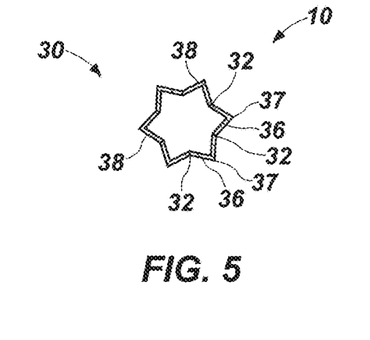
FIG. 5 is a circumferential cross-sectional representation of the expandable section of the exoskeleton device, taken transverse to a longitudinal axis of the exoskeleton device, with the expandable section in an partially expanded state.

As illustrated by FIGS. 1-4, when the expandable section 30 is in its unexpanded state, the outer surface $13_O$ of the wall 13 of the portion of the body 12 from which the expandable section 30 is defined may be substantially smooth, accounting for discontinuities that occur as material is removed from the wall 13 of the body 12 to form each slit 32. As illustrated by FIG. 5, as the expandable section 30 starts to expand, the slits 32 open up. The slits 32 may open up into a diamond shape or into a shape that resembles a diamond. As the slits 32 open up, the struts 36 may rotate from circumferentially disposed orientations (i.e., where the outer surface $13_O$ of each strut 36 is oriented along the circumference of the wall 13 of the body 12) to more radial orientations. All of the struts 36 of the expandable section 30 may rotate in the same direction (e.g., counterclockwise, etc.). Junctions between circumferentially adjacent struts 36 may also rotate from circumferentially disposed orientations to more radial orientations (e.g., without folding, etc.). As each strut 36 begins to rotate, an edge 37 of the strut 36 is exposed at an outer extent of the expanded expandable section 30. FIG. 5 shows the expandable section 30 in a partially expanded state, or an intermediate state.

Figure 6:
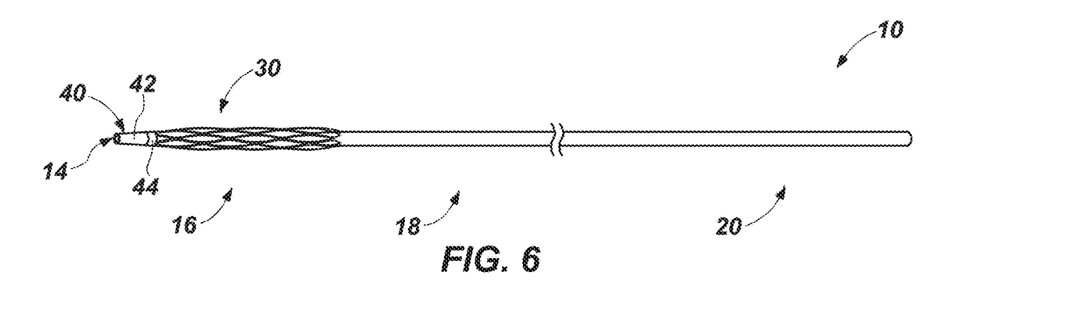
FIG. 6 illustrates the embodiment of the exoskeleton device shown in FIG. 1, showing the expandable section in an expanded state.
Figure 7:
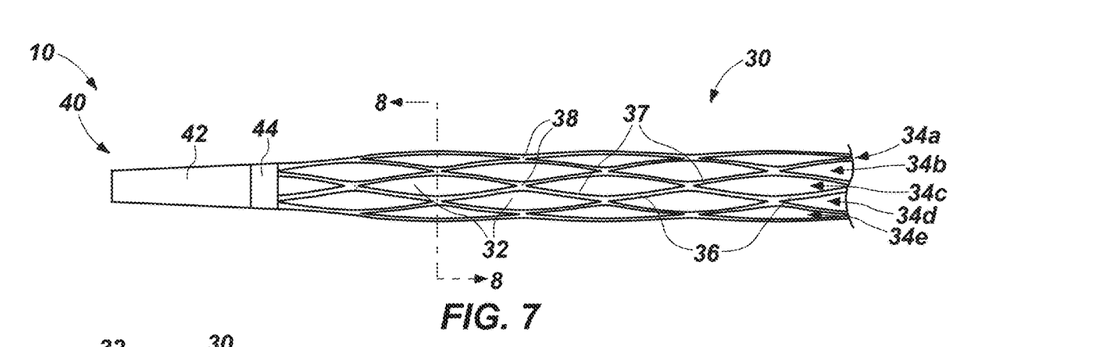
FIG. 7 provides an enlarged side view of the expandable section of the exoskeleton device in the expanded state.
Figure 8:
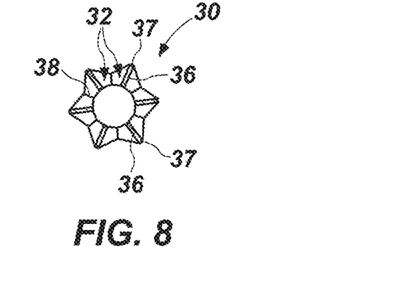
FIG. 8 provides a circumferential cross-sectional view through the expandable section in the expanded state, taken along line 8-8 of FIG. 7.

FIGS. 6-8 depict the expandable section 30 of the exoskeleton device 10 in a fully expanded state. As illustrated by FIG. 8, when the expandable section 30 is fully expanded, each strut 36 may rotate by as much as 90°, with each strut 36 being oriented substantially radially. When the expandable section 30 is in an expanded state (i.e., partially expanded, fully expanded, etc.), the struts 36 and their at least partially outward facing edges 37 may be forced against the location that is to be treated, which may also be referred to herein as a treatment site. As the members of the expandable section 30 are forced against the location that is to be treated, the members of the expandable section 30 may contact that location or even score that location. In embodiments where the members of the expandable section 30 carry a medicament, the medicament may be transferred from the struts 36 to the location that has been treated. The medicament may also be introduced into any scores formed at the location that has been treated.

FIGS. 1-8 illustrate an embodiment of expandable section 30 that includes straight slits 32. Exoskeleton devices whose expandable sections include slits with other orientations and configurations, such as those depicted by FIGS. 9-16, are also within the scope of this disclosure.

Figure 9:
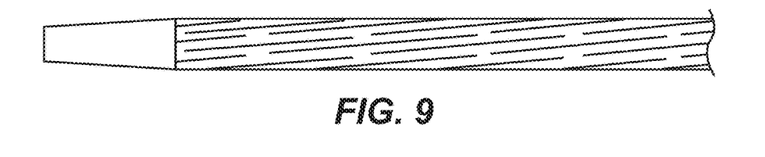
FIG. 9 provides an enlarged side view of an embodiment of expandable section of an exoskeleton device with helically oriented slits and struts, showing the expandable section in an unexpanded state.

As illustrated by FIG. 9, as an alternative to the longitudinally oriented slits 32 and struts 36 depicted by FIGS. 1-8, the slits 132 and struts 136 in the body 112 of an expandable section 130 of an exoskeleton device 110 may be oriented helically or spirally around the circumference of the body 112. In a specific but nonlimiting embodiment, the slits 132 may be arranged along a line that spirals 180° around the circumference of the body 112 of the exoskeleton device 110 every 5 cm. The spirals and, thus, the slits 132 arranged along each spiral, may be positioned 0.018 inch apart from one another over the circumference of the body 112 of the exoskeleton device 110. The body 112 of the exoskeleton device 112 (e.g., a hypotube, etc.) may have a thickness of 0.0025 inch.

Figure 10:
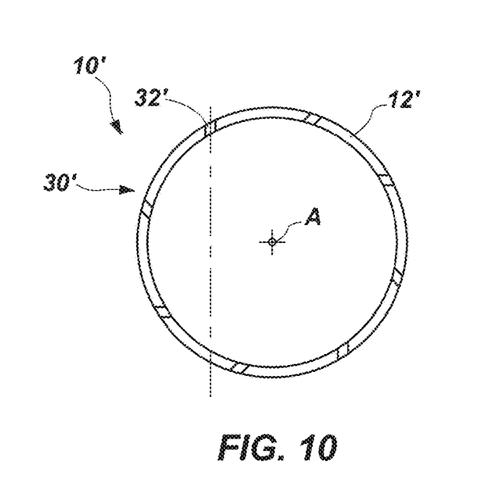
FIGS. 10 and 11 provide circumferential cross-sectional views through other embodiments of expandable sections of exoskeleton devices, with the expandable sections in unexpanded states.
Figure 11:
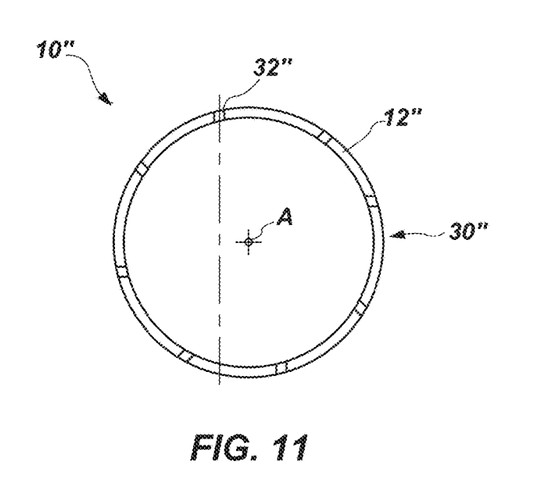
Figure 12:
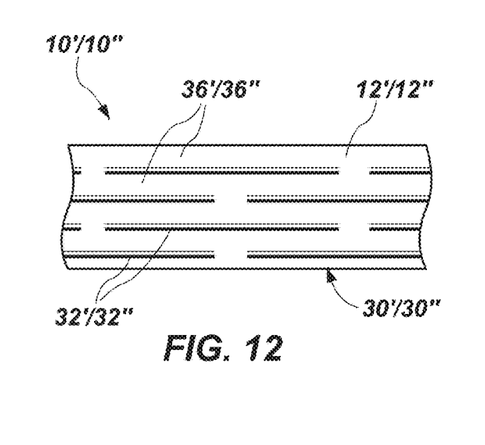
FIG. 12 is a partial side view representing the expandable sections of FIGS. 10 and 11 in unexpanded states.
Figure 13:
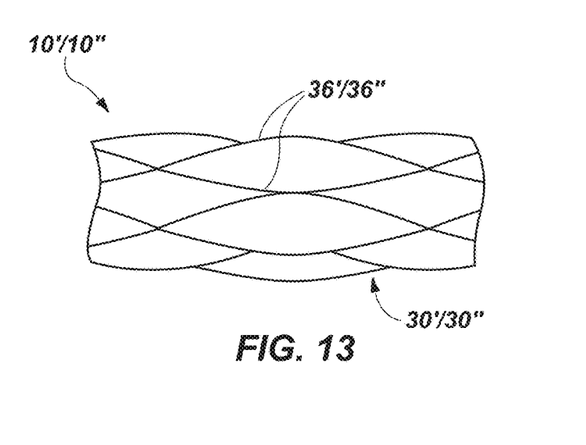
FIG. 13 is a partial side view representing the expandable sections of FIGS. 10 and 11 in expanded states.

FIGS. 10 and 11 show embodiments of slits 32' and 32" defined by one or more cuts that are oriented non-radially, or off-axis A through the portion of the body 12', 12" from which the expandable section 30', 30" of an exoskeleton device 10', 10" is defined. Such cuts may define a slit 32', 32" with an edge has an acute corner. Such an edge may resemble a blade or comprise a blade. FIG. 12 provides a partial side view of the relaxed, circumferentially oriented struts 36', 36" defined by such slits 32', 32" with the expandable section 30', 30" in an unexpanded state. FIG. 13 provides a partial side view of the radially rotated struts 36', 36" the expandable section 30', 30" in an expanded state.

In other embodiments, the struts of an exoskeleton device according to this disclosure may be defined by non-linear slits. As an example, a slit that is located between and partially defines two struts may define one or more cutouts in one of the struts (e.g., one or more curved cutouts, one or more trapezoidal cutouts, etc.). The recesses may improve flexibility and/or allow for suction or injection between struts. Optionally, the same slit may define a protrusion (e.g., a serration, a tooth, a barb, etc.) in the other strut.

Figure 14:
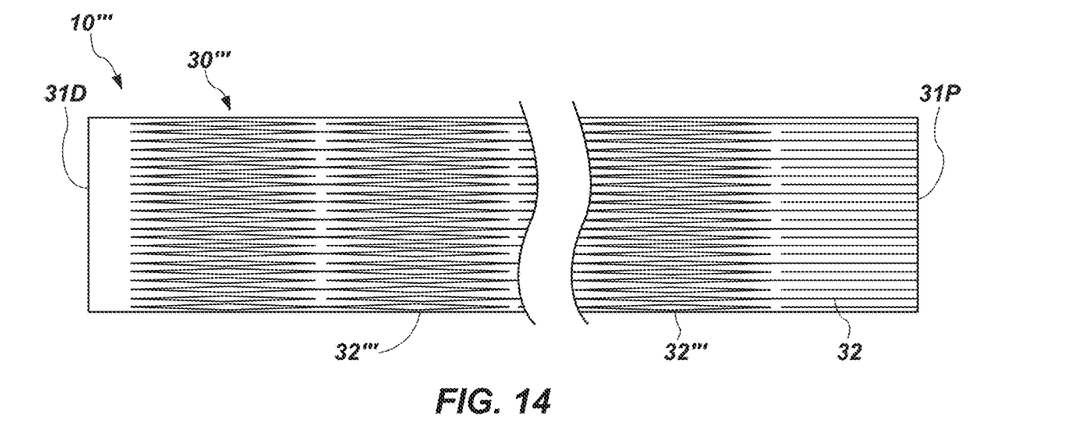
FIG. 14 provides an enlarged side view of yet another embodiment of expandable section of an exoskeleton device, with the expandable section in an unexpanded state.

In a specific embodiment, an expandable section 30''' of an exoskeleton device 10''' may include slits 32''' that have open shapes. For example, one or both of the long edges of such a slit 32''' may include one or more recesses (e.g., a concave curvature, a recess defined by two or more straight edges, etc.). FIG. 14 depicts a specific, but nonlimiting embodiment of slit 32''' that has a smooth diamond shape or a double smooth diamond shape defined by elongated concavely curved cuts.

The distances across the gaps of embodiments of slits 32''' with open shapes may limit the distance that the rotated struts 36''' defined by such slits 32''' may protrude and score a surface against and into which the rotated struts 36''' are forced. The open shape of a slit 32''' may improve flexibility of the expandable element 30''' (e.g., while in its unexpanded state, etc.). The open shape of a slit 32''' may enable for suction and/or infusion between struts 36'''.

In some embodiments, such as that depicted by FIG. 14, an expandable section 30''' may include a combination of differently shaped slits 32, 32''' (e.g., straight slits 32 and double diamond shaped slits 32", etc.). As an example, straight slits 32 may be located at one or both ends 31P and 31D of the expandable section 30''', although FIG. 14 shows straight slits 32 as being located adjacent to end 31P. Shaped slits 32''' may be located at intermediate locations along the length of the expandable section 30''' and adjacent to one or both ends 31P and 31D of the expandable section 30'''.

Figure 15:
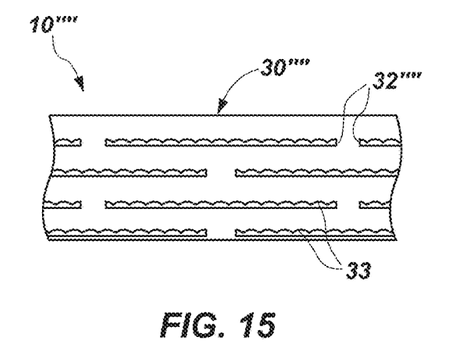
FIG. 15 is a partial side view representing an expandable section of an embodiment of an exoskeleton device in an unexpanded state, the expandable section including struts with features on the edges thereof.
Figure 16:
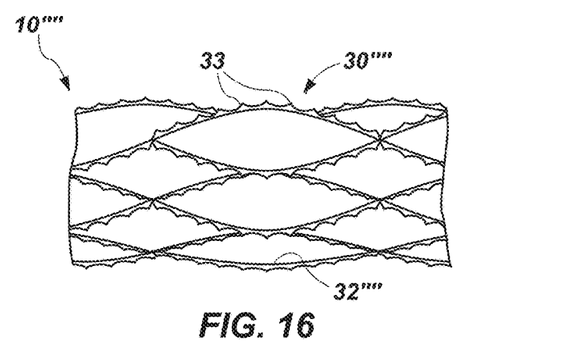
FIG. 16 is a partial side view representing the expandable section of FIG. 15 in an expanded state.

FIGS. 15 and 16 depict an embodiment of an exoskeleton device 10'''' with an expandable section 30'''' that includes slits 32''' with serrations 33, or teeth. FIG. 15 illustrates the expandable section 30'''' in an unexpanded state, while FIG. 16 shows the expandable section 30'''' in an expanded state.

Of course, exoskeleton devices that with expandable sections that are defined by slits of other configurations are also within the scope of this disclosure.

Turning now to FIGS. 17-24, an exoskeleton device 210, 210', 210", 210''' may include an expandable section 230, 230', 230", 230''' that carries a medicament 250 (e.g., a drug, another substance, etc.). The medicament 250 may be eluted or otherwise delivered to a surface (e.g., pathology, tissue, etc.) upon engagement (e.g., contact, scoring, etc.) of that surface by struts 236 (e.g., the embodiments of struts disclosed herein, other embodiments of struts, etc.).

Figure 17:
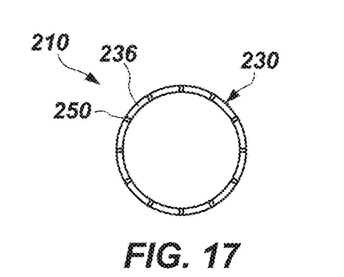
FIG. 17 is a cross-sectional representation of an expandable section of an embodiment of an exoskeleton device in an unexpanded state, the edges of struts of the expandable section carrying a medicament.
Figure 18:
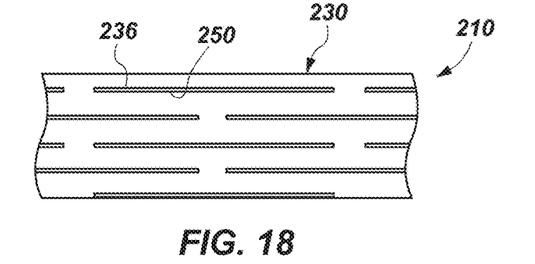
FIG. 18 is a partial side view representing the expandable section of FIG. 17 in an unexpanded state.

As illustrated by FIGS. 17 and 18, the medicament 250 may be carried by the edges of struts 236, which edges are defined by the slit 232. The medicament 250 may be coated directly onto the edges of the struts 236 (e.g., in a solid form, etc.) (e.g., on the edges, within recesses of a texture of the edges, etc.). Alternatively, the medicament 250 may be carried indirectly by the edges of the struts 236, such as by absorbent elements on the edges of the struts 236. Upon advancement of the expandable section 230 to a desired location within a subject's body, expansion of the expandable section 230 or a portion thereof, and optionally causing one or more struts 236 of the expandable section 230 to score a surface at the desired location, the medicament 250 may be delivered to the surface and into any score marks that have been formed.

Figure 19:
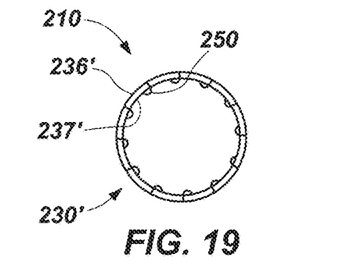
FIG. 19 is a cross-sectional representation of an expandable section of another embodiment of an exoskeleton device in an unexpanded state, interior surfaces of struts of the expandable section carrying a medicament.
Figure 20:
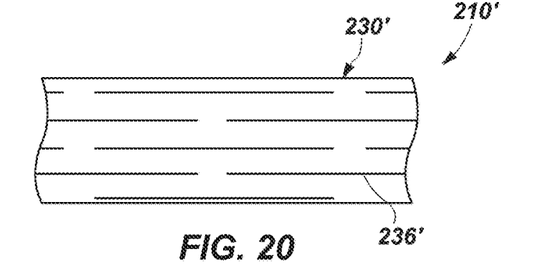
FIG. 20 is a partial side view representing the expandable section of FIG. 17 in an unexpanded state.

In addition, or as an alternative, as depicted by FIGS. 19 and 20, the medicament 250 may be carried on an interior surface 237' of each strut 236' at a location adjacent to an edge of the strut 236' and, thus, at a location adjacent to the slit 232' that defines the strut 236'. By applying the medicament 250 to interior surfaces 237' of the struts 236', the medicament 250 may be protected and its introduction into the body of a subject may be prevented until the expandable section 230' is advanced to the location where the medicament 250 is to be administered and expanded at that location. Such a configuration may be useful for delivering drugs that may be harmful or present mortality issues when improperly administered (e.g., paclitaxel, etc.). Upon expansion of the expandable section 230' or a portion thereof and causing one or more struts 236' of the expandable section 230' to engage that surface, the medicament 250 may be delivered to the surface and into any score marks that have been formed.

Figure 21:
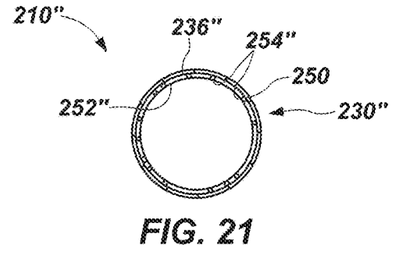
FIG. 21 is a cross-sectional representation of an expandable section of an embodiment of an exoskeleton device in an unexpanded state, a porous polymeric film lining an interior surface of the expandable section carrying a medicament.
Figure 22:
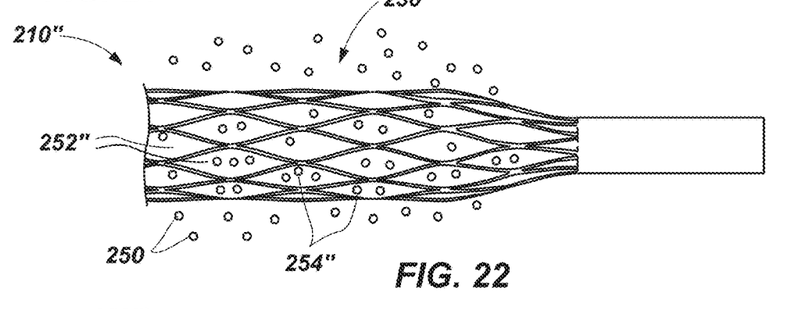
FIG. 22 is a partial side view representing the expandable section of FIG. 22 in an expanded state.

As an alternative to having the struts carry the medicament, the expandable element may include a polymeric film that carries the medicament. As an example, and as depicted by FIG. 21, a porous polymeric film 252" may internally line the unrotated struts 236" of an expandable section 230" of an exoskeleton device 210". Such a porous polymeric film 252" may include pores 254" that carry and retain the medicament 250 while the porous polymeric film 252" remains in a relaxed state, but release the medicament 250 when the struts 236" are forced radially outward and the porous polymeric film 252" is stretched, as shown in FIG. 22.

Figure 23:
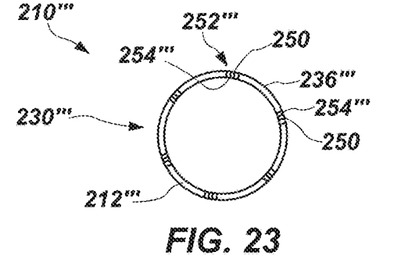
FIG. 23 is a cross-sectional representation of an expandable section of another embodiment of an exoskeleton device in an unexpanded state, porous polymeric films that carry a medicament extending across gaps between circumferentially adjacent struts of the expandable section.
Figure 24:
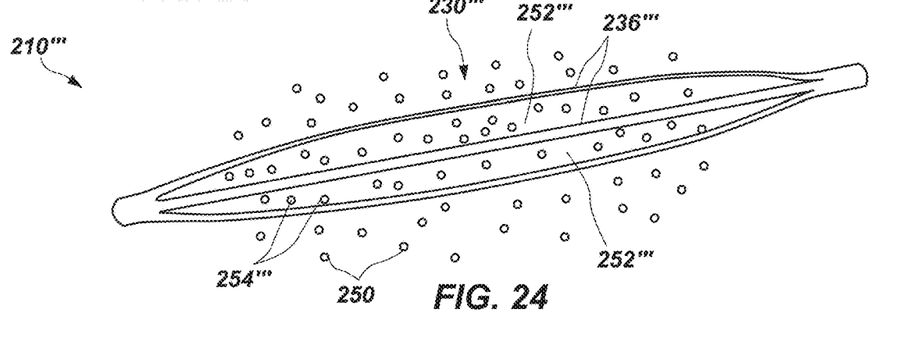
FIG. 24 is a partial side view representing the expandable section of FIG. 23 in an expanded state.

As another example, FIGS. 23 and 24 illustrate an embodiment of exoskeleton device 210''' with an expandable section 230''' that includes struts 236''' that are circumferentially spaced apart from one another. A porous polymeric film 252''' extends across the gaps between adjacent struts 236'''. The porous polymeric film 252''' includes pores 254''' that carry the medicament 250. Upon expansion of the expandable section 230''', adjacent struts 236''' may be forced apart from one another, optionally rotate, and stretch the porous polymeric film 252''', opening the pores 254''' to an extent that may release the medicament 250 from the pores 254''' and, thus, deliver the medicament 250 to the site where the expandable section 230''' of the exoskeleton device 210''' is located.

Embodiments of an exoskeleton device 210''' having the configuration shown in FIGS. 23 and 24 but lacking a porous polymeric film 252''' are also within the scope of this disclosure. The struts 236''' of such an exoskeleton device 210''' may extend along the entire length of the expandable section 230''' of the exoskeleton device 210'''. In a specific, but non-limiting embodiment, the body 212'' of such an exoskeleton device 210''' may comprise a tube (e.g., a hypotube, etc.) with a thickness of 0.0025 inch with six struts 236''' positioned around its circumference. When the expandable section 230''' of the exoskeleton device 210''' expands, the struts 236''' may not rotate; thus, the expanded expandable section 230''' of the exoskeleton device 210''' may not cut the surface against which it is positioned.

The porous polymeric films 252'', 252''' of the embodiments of exoskeleton device 210'', 210''' depicted by FIGS. 21-24 may comprise a material such as PET, PTFE, or the like. The pores 254'', 254''' may be formed or defined in the porous polymeric film 252'', 252''' in any suitable manner. Medicament may be introduced into the pores 254'', 254''' as the pores 254'', 254''' are formed or after they are formed.

Figure 1:
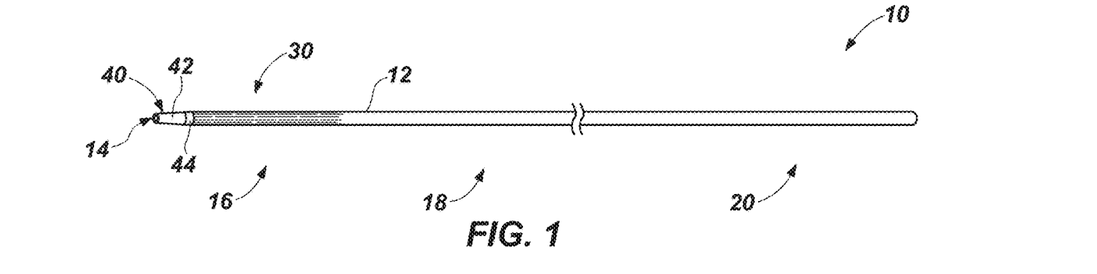
FIG. 1 illustrates an embodiment of an exoskeleton device according to this disclosure, showing an expandable section of the exoskeleton device in an unexpanded state, or a relaxed state.
Figure 2:
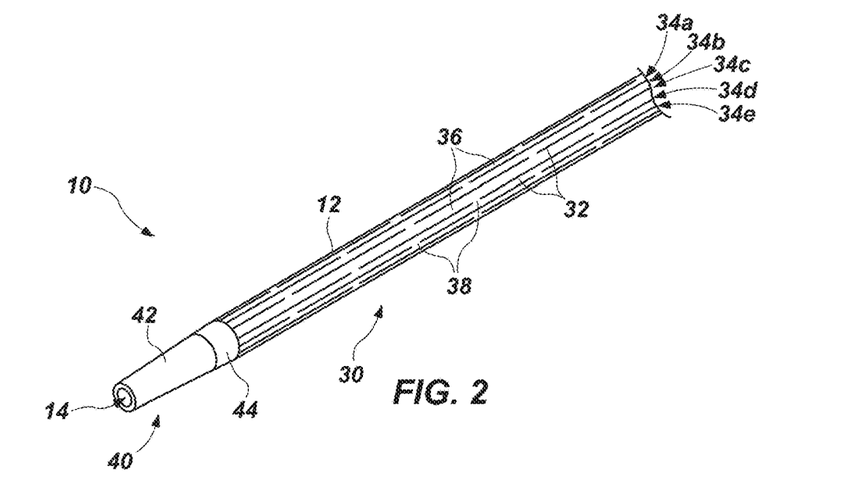
FIG. 2 provides an enlarged orthogonal view of the expandable section of embodiment of exoskeleton device shown in FIG. 1, with the expandable section in the unexpanded state.

With returned reference to FIGS. 1 and 6, a distal end 40 of the exoskeleton device 10 (or any other embodiment of exoskeleton device within the scope of this disclosure) may have a configuration that enables its introduction into a subject's body (e.g., into a vessel within the body of a subject, etc.) and its advancement through the subject's body. In some embodiments, the distal end 40 of the exoskeleton device 10 may have a frustoconical configuration (i.e., it may have the shape of a truncated cone, which lacks a pointed tip). Alternatively, the distal end 40 may comprise an open sheath with a slightly tapered outer surface but an inner surface that is not reduced, which may optimize the flow of fluids out of an into the distal end 40. The tapers of distal ends 40 with such configurations may be gradual (e.g., a taper of about 5°, a taper of about 8°, a taper of about 10°, etc.).

A collar 42 may be provided at the distal end 40 of the exoskeleton device 10 and/or at a distal side of the expandable section 30 of the exoskeleton device 10. The collar 42 may facilitate introduction of the exoskeleton device 10 into a subject's body, as well as advancement of the exoskeleton device 10 through the subject's body. Such a collar 42 may be smooth and, optionally, flexible (e.g., it may be formed from a flexible, resilient material, such as silicone, etc.). In some embodiments, the collar 42 may be provided around a distal end of the expandable section 30 to limit expansion at the distal end of the expandable section 30.

Figure 25:
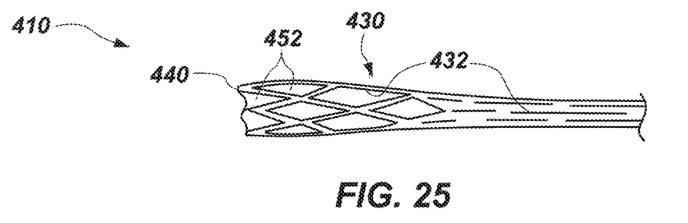
FIG. 25 illustrates a distal portion of an embodiment of an exoskeleton device with an expandable element that extends to the distal end of the exoskeleton device, with the distal end of the expandable element in an expanded state.

Alternatively, as depicted by FIG. 25, the expandable section 430 of an exoskeleton device 410 may extend to the distal end 440 of the exoskeleton device 110. Such a configuration may enable the distal end 440 to be expanded (e.g., to the shape of a funnel and, thus, use of the distal end of the exoskeleton device as a funnel). The inclusion of an expandable film 452 around, inside, or within the slits 432 of the expandable section 430 at the distal end 440 or may impart the expandable section 430 with further functionality. For example, the expandable film 452 may enable use of the distal end 440 of the expandable section 430 (e.g., a distal end 440 that has been expanded into the shape of a funnel, etc.) to aspirate material, or the like. The exoskeleton device 410, or at least its expandable section 430, and any expandable film 452 carried by the expandable section 430, may be capable of retaining the expanded shapes (e.g., funnel shapes, etc.) into which they are formed. These may include the use of some metals, metal alloys, or polymers for use in forming the expandable section 430 and some stretchable polymers and/or polymers or fabrics that may be alternately gathered and held taught for use in forming the expandable film 452.

Returning reference again to FIGS. 1 and 6, a radiopaque marker 44 may be provided at the distal end 40 of the exoskeleton device 10. The distal end 40 may be formed from a radiopaque material (e.g., platinum, etc.) to define the radiopaque marker 44, or a band of radiopaque material may be placed at or near the distal end 40 of the exoskeleton device 10 (e.g., directly adjacent to a distal side of the expandable section 30, etc.). The radiopaque marker 44 may enable visualization (e.g., through fluoroscopy, etc.) of a location of the exoskeleton device 10 and/or its expandable section 30 within a subject's body.

With continued reference to FIGS. 1 and 6, the intermediate portion 18 of the exoskeleton device 10 is located on a proximal side of the expandable section 30, and the proximal portion 20 of the exoskeleton device 10 is located on a proximal side of the intermediate portion 18, closest to an individual (e.g., a healthcare professional, etc.) introducing, advancing, and/or operating the exoskeleton device 10 and any associated devices.

The intermediate portion 18 and/or the proximal portion 20 of the exoskeleton device 10 may be capable of receiving and/or otherwise engaging one or more other elongated medical instruments (e.g., a guide wire, one or more expandable instruments, etc.) (not shown in FIGS. 1-8), including elongated medical instruments that are capable of expanding the expandable section 30 of the exoskeleton device 10 and other medical devices with which the exoskeleton device 10 may be used. In some embodiments, the intermediate portion 18 and, optionally, the proximal portion 20 of the exoskeleton device 10 may comprise a tubular element coextensive with a proximal side of the expandable section 30. The tubular element may include a lumen that can receive the one or more other elongated medical instruments. In some embodiments, the intermediate portion 18 and, optionally, the proximal portion 20 of the exoskeleton device 10 may comprise an extension of the body 12 of the exoskeleton device 10. Alternatively, the proximal portion 20 and, optionally, the intermediate portion 18 of the exoskeleton device 10 may comprise another separately manufactured structure (e.g., a catheter, another tube, a tether, etc.) that may be aligned with and is secured to a proximal end of the body 12 of the exoskeleton device 10.

Figure 26:
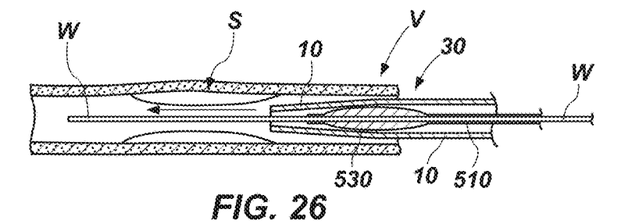
FIG. 26 is a cross-sectional representation showing an embodiment of a technique for introducing an expandable section of an exoskeleton device to a target location within a body of a subject, in which the exoskeleton device and an expandable instrument are pre-assembled with an expandable section of the exoskeleton device positioned over an expander of the expandable instrument, and then the expandable section and the expander are introduced to the target location together in an assembled relationship.
Figure 27:
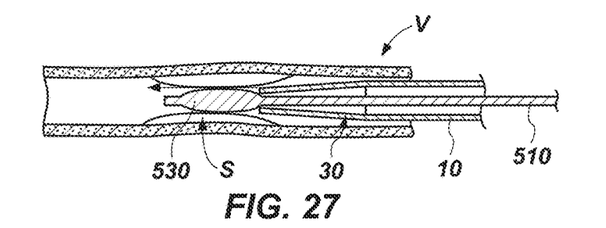
FIG. 27 is a cross-sectional representation showing another embodiment of a technique for introducing an expandable section of an exoskeleton device to a target location within a body of a subject, in which an expander of an expandable instrument is introduced to the target location, and then the exoskeleton device is introduced into the body over the expandable instrument until an expandable section of the exoskeleton device is positioned over the expander of the expandable instrument at the target location.
Figure 28:
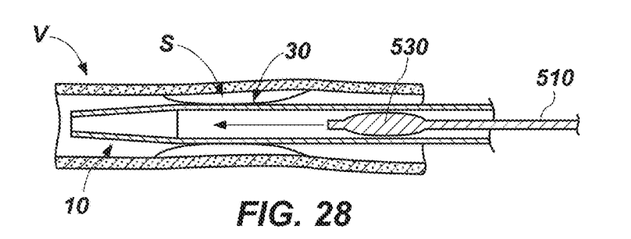
FIG. 28 is a cross-sectional representation showing yet another embodiment of a technique for introducing an expandable section of an exoskeleton device to a target location with a body of a subject, in which the exoskeleton device is introduced into the body of a subject until an expandable section of the exoskeleton device reaches a target location, and then an expandable instrument is introduced into the body through a lumen of the exoskeleton device, until an expander of the expandable instrument is positioned within the expandable section of the exoskeleton device.

Turning now to FIGS. 26-28, embodiments of various techniques for introducing an exoskeleton device 10 (FIGS. 1-8) or any other embodiment of exoskeleton device within the scope of this disclosure into a body of a subject are depicted.

In FIG. 26, an embodiment of a technique for introducing an expandable section 30 of an exoskeleton device 10 to a treatment site S, or a target location, within a body of a subject is shown. In that method, a guide wire W is introduced into the subject's body and advanced to and, optionally, through the treatment site S in a manner known in the art. The treatment site S shown in FIG. 26 is a narrowed or occluded location along a vessel V (e.g., a blood vessel, such as an artery or a vein, etc.); it should be noted, however, that the expandable section 30 of the exoskeleton device 10 may be used to treat other organs or features of a subject's anatomy. In FIG. 26, the exoskeleton device 10 and an expandable instrument 510 are pre-assembled, with an expandable section 30 of the exoskeleton device 10 positioned over an expander 530 of the expandable instrument 510. Preassembly of the exoskeleton device 10 and the expandable instrument 510 may include securing the exoskeleton device 10 to the expandable instrument 510. The exoskeleton device 10 and the expandable instrument 510 may then be placed over the guide wire W and introduced into the subject's body together (i.e., simultaneously), and advanced along the guide wire W until the expandable section 30 and the expander 530 reach the treatment site S.

FIG. 27 illustrates another embodiment of a technique for introducing an expandable section 30 of an exoskeleton device 10 to a treatment site S within a subject's body. In the method depicted by FIG. 27, a guidewire W (FIG. 14) is first introduced into the subject's body and advanced through the subject's body to and, optionally, through the treatment site S. With the guidewire W in place, an expandable instrument 510 may then be introduced into the subject's body and advanced through the subject's body until an expander 530 at or near a distal end of the expandable instrument 510 reaches the treatment site S. With the expander 530 at the treatment site S, the guidewire W may, in some embodiments, be removed from the expandable instrument 510 and, thus, from the subject's body. The exoskeleton device 10 may be positioned over the expandable instrument 510 (e.g., a proximal end of the expandable instrument 510 may be placed in a lumen 14 (FIGS. 1 and 4) of the exoskeleton device 10, etc.) and, if the guidewire W remains in place, over the guidewire W. The exoskeleton device 10 may then be introduced into the subject's body and advanced over the expandable instrument 510, through the subject's body until the expandable section 30 is positioned over the expander 530 and at the treatment site S.

FIG. 28 depicts an embodiment of an exoskeleton device 10 introduction and advancement method that includes introducing a guidewire W (FIG. 16) into the subject's body, advancing the guidewire W through the subject's body to the treatment site S, and, optionally, advancing the guidewire W through the treatment site S. With the guidewire W in place, the exoskeleton device 10 may then be introduced into the subject's body and advanced through the subject's body until an expandable section 30 of the exoskeleton device 10 reaches the treatment site S. With the expandable section 30 at the treatment site S, the guidewire W may, in some embodiments, be removed from the exoskeleton device 10 and, thus, from the subject's body. An expandable instrument 510 may be assembled with a proximal portion 20 (FIGS. 1 and 6) of the exoskeleton device 10 (e.g., introduced into a lumen 14 (FIGS. 1 and 4) of the exoskeleton device 10, etc.), and then advanced into the subject's body along the exoskeleton device 10 (e.g., through the lumen 14 of the exoskeleton device 10, etc.), until an expander 530 of the expandable instrument 510 is positioned at a desired location within the expandable section 30 of the exoskeleton device 10 and, thus, at the treatment site S.

Figure 29:
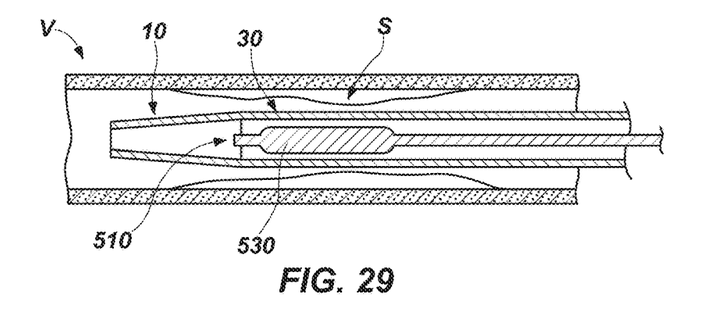
FIG. 29 is a cross-sectional representation showing an embodiment of an expander of an expandable instrument within an embodiment of an expandable section of an exoskeleton device, with the expander and the expandable section in unexpanded, or relaxed, states.
Figure 30:
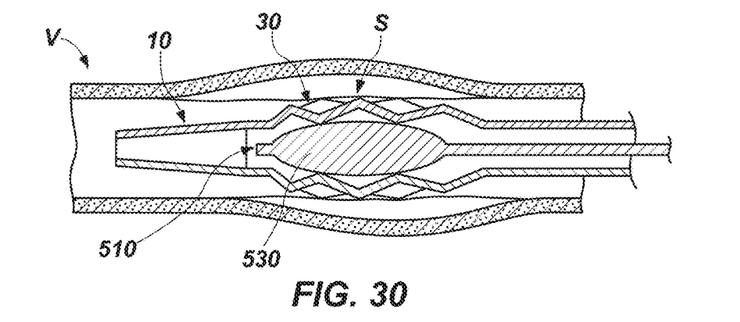
FIG. 30 is a cross sectional representation showing the embodiments of expander and expandable section of FIG. 29 in expanded states.

Regardless of how the expandable section 30 of the exoskeleton device 10 is introduced to the treatment site S and over the expander 530 of the expandable instrument 510, with the expandable section 30 of the exoskeleton device 10 at the treatment site S and the expander 530 of the expandable instrument 510 within the expandable section 30, as shown in FIG. 29, the expander 530 may be expanded in a suitable manner to expand the expandable section 30 (e.g., a balloon of a balloon catheter may be inflated, etc.), as illustrated by FIG. 30. With added reference to FIGS. 5 and 6-8, expansion of the expandable section 30 may cause edges 37 of the struts 36 of the expandable section 30 to contact and, optionally, score locations of the treatment site S (e.g., a diseased site, such as the site of an atherosclerotic plaque or the like; a wounded site; etc.) against which the edges 37 of the struts 36 are forced.

In embodiments such as that depicted by FIG. 28, a plurality of different expandable instruments 510 with differently configured expanders 530 (e.g., balloon catheters with balloons that expand to increasingly larger diameters, etc.) may be sequentially introduced to a treatment site S, operated (or used), and removed from the treatment site S through a single, previously placed exoskeleton device 10. As the expander 530 of an expandable instrument 510 is expanded, it expands the expandable section 30 of the exoskeleton device 10. As the expandable section 30 expands, struts 36 of the expandable section 30 may rotate, outwardly, as shown in FIGS. 5-7. Upon rotating, the struts 36 may engage adjacent tissue (e.g., an interelastic layer (IEL) of a blood vessel (e.g., an artery, a vein, etc.). The extent to which each strut 36 engages the tissue depends upon the width of each strut 36 and the extent to which it rotates as the expandable section 30 expands. In some embodiments, the struts 36 of an expandable section may score or pierce adjacent tissue to a depth of 0.25 mm or more (e.g., 0.50 mm, 0.75 mm, etc.). The number of struts 36 around the circumference of the expandable section 30 (e.g., 8, 10, 12, 14, 16, 18, 20, 22, 24, 26, etc.) may define the number of score marks or cuts that can be made in the tissue with a single pass, or expansion, of the expandable section 30. In embodiments where the adjacent tissue comprises the IEL of a blood vessel, such scoring or piercing may safely injure the IEL, enabling more effective drug delivery than that realized by the use of conventional scoring balloon catheters.

With the expandable section 30 of the exoskeleton device 10 partially or fully expanded at the treatment site S, the exoskeleton device 10 and its expandable section 30 may be rotated continuously or in an oscillating, or alternating manner. Such rotation of the partially or fully expanded expandable section 30 may break up pathology (e.g., thrombus, atheroma, etc.) or affect tissue in a manner that will prepare it for infusion of a medicament or another substance.

As another option, the expandable section 30 may be advanced to and partially or fully expanded at a location past, or distal to, the treatment site S. The at least partially expanded expandable section 30 may then be pulled proximally to and, optionally, through the treatment site S. By manipulating the exoskeleton device 10 and moving its expandable section 30 in such a way, the outwardly rotated edges of the struts 36 may create linear scores in surfaces (e.g., pathology, tissue, etc.) at the treatment site S.

As another option, a medicament or another substance may be delivered to the treatment site S prior to, during, or after expanding the expandable section 30. The medicament or other substance may be delivered by infusion through the exoskeleton device 10, from the expandable section 30 (e.g., by elution, etc.) (see, e.g., FIGS. 17-24 and associated disclosure), or by infusing a fluid (e.g., a gas, saline, etc.)

over a medicament carried by the surface of the expander 530 of the expandable instrument 510.

In embodiments where infusion occurs and the expander 530 comprises a balloon, the medicament or other substance may be delivered distally (i.e., to the treatment site S) if the expander 530 is only partially expanded but, when the expander 530 is fully expanded, the medicament or other substance may only be delivered to locations proximal to the treatment site S.

The exoskeleton device 10 may be connected to active suction throughout a procedure to pull pathology (e.g., atherectomy, etc.), thrombi, emboli, etc., between the struts 36 before, during, or after inflation.

Once use of an expander 130 of an expandable instrument 110 is complete, pressure within the expander 130 may be released. The release of pressure within the expander 130 may enable the expandable section 30 to collapse over the expander 130. As the expandable section 30 collapses, the expander 130 may also collapse, or re-wrap, which may facilitate its removal from within the expandable section 30, as well as reintroduction of the expander 130 back into its sheath and, thus, its removal from the exoskeleton device 10 and, thus, from the body of the subject. Thereafter, another medical instrument may be introduced into the body through the exoskeleton device 10. As an example, an expandable instrument 110 with a larger expander 130 may be introduced into the exoskeleton device 10 and used in a manner that expands the expandable section 30 even further (i.e., to a larger radius).

Although the foregoing description provides many specifics, these should not be construed as limiting the scopes of any of the appended claims, but merely as providing information pertinent to some specific embodiments that may fall within the scopes of the appended claims. Features from different embodiments may be employed in combination. In addition, the scopes of the appended claims may encompass other embodiments. All additions to, deletions from, and modifications of the disclosed subject matter that fall within the scopes of the claims are to be embraced by the claims.

What is claimed:

1. An exoskeleton device advanceable over a balloon catheter, comprising: an expandable section advanceable over a balloon of the balloon catheter, the expandable section including a plurality of struts, each strut extending along a length of the expandable section with the plurality of struts being positioned around a circumference of the expandable section, each strut of the plurality of struts having a longitudinal axis and including a plurality of sections, each section defined by a pair of parallel slits through the expandable section, each slit of the pair of parallel slits separating the section of a strut of the plurality of struts from an adjacent section of an adjacent strut of the plurality of struts, an arrangement of slits of the expandable section rendering the expandable section radially expandable in a manner that rotates each strut about the longitudinal axis of the strut to enable the strut to score a tissue adjacent to the strut, each strut including an interior surface and a scoring edge, the interior surface of the strut carrying a medicament, the medicament being contained within the expandable section while the strut is in a closed orientation and exposed to an environment outside the expandable section and deliverable to a score mark formed in the tissue by the strut when the strut is in an open orientation.

2. The exoskeleton device of claim 1, wherein an outer surface of the expandable section is substantially smooth when the expandable element is in an unexpanded state.

3. The exoskeleton device of claim 1, wherein the scoring edge comprises a blade.

4. The exoskeleton device of claim 1, wherein the scoring edge comprises teeth.

5. An exoskeleton device advanceable over a balloon catheter, comprising: an expandable section advanceable over a balloon of the balloon catheter, the expandable section including a plurality of struts, each strut extending along a length of the expandable section with the plurality of struts being positioned around a circumference of the expandable section, each strut of the plurality of struts having a longitudinal axis and including a plurality of sections, each section defined by a pair of parallel slits through the expandable section, each slit of the pair of parallel slits separating the section of a strut of the plurality of struts from an adjacent section of an adjacent strut of the plurality of struts, an arrangement of slits of the expandable section rendering the expandable section radially expandable in a manner that rotates each strut about the longitudinal axis of the strut to enable the strut to score a tissue adjacent to the strut, the plurality of struts including interior surfaces; and a medicament carried by the interior surfaces of the plurality of struts of the expandable section, contained within the expandable section while the plurality of struts are in closed orientations, and exposed to an environment outside the expandable section and deliverable to a score mark formed in the tissue by the strut when the plurality of struts are in open orientations.

6. The exoskeleton device of claim 5, wherein the medicament is carried by an edge of each strut.

7. The exoskeleton device of claim 5, wherein the medicament is carried by an interior surface of the strut at a location adjacent to an edge of each strut.

8. The exoskeleton device of claim 5, further comprising: a porous polymeric film carrying the medicament.

9. The exoskeleton device of claim 8, wherein the porous polymeric film coats an interior surface of the expandable section.

10. The exoskeleton device of claim 8, wherein the porous polymeric film extends across slits of the expandable section.

11. The exoskeleton device of claim 5, wherein struts of the plurality of struts of the expandable section include scoring edges.

12. The exoskeleton device of claim 11, wherein the scoring edges comprise blades.

13. The exoskeleton device of claim 11, wherein the scoring edges comprise teeth.

14. A method for delivering a medicament to a treatment site within a body of a subject, comprising: advancing an exoskeleton device over a balloon catheter until an expandable section of the exoskeleton device is located over a balloon of the balloon catheter, with the medicament located on interior surfaces of struts of the expandable section and with the struts in closed orientations that contain the medicament within an interior of the expandable section; expanding the balloon to expand the expandable section of the exoskeleton device in a manner that causes struts of the expandable section to move to open orientations and rotate about their longitudinal axes to score a surface at the treatment site and expose the medicament on the interior surfaces of the struts to the treatment site; and transferring the medicament from the interior surfaces of the struts of the expandable section to score marks in the surface at the treatment site.

15. The method of claim 14, wherein expanding the balloon to expand the expandable section releases the medicament from pores of a porous polymeric film of the expandable section.

* * * * *